(12) United States Patent
Viertl et al.

(10) Patent No.: US 7,064,825 B2
(45) Date of Patent: Jun. 20, 2006

(54) METHODS AND APPARATUS FOR EVALUATING ROTARY MACHINERY

(75) Inventors: John Ruediger Mader Viertl, Niskayuna, NY (US); Tymm Bradner Schumaker, Saratoga Springs, NY (US)

(73) Assignee: General Electric Company, Schenectady, NY (US)

( * ) Notice: Subject to any disclaimer, the term of this patent is extended or adjusted under 35 U.S.C. 154(b) by 409 days.

(21) Appl. No.: 10/722,298

(22) Filed: Nov. 25, 2003

(65) Prior Publication Data

US 2005/0110991 A1    May 26, 2005

(51) Int. Cl.
*G01J 3/30* (2006.01)
(52) U.S. Cl. .................... 356/318; 219/121.6
(58) Field of Classification Search ........ 356/317–334; 219/121.83, 121.85, 121.6; 73/11.02, 659, 73/660, 602
See application file for complete search history.

(56) References Cited

U.S. PATENT DOCUMENTS

| | | |
|---|---|---|
| 4,543,486 A | 9/1985 | Rose |
| 4,634,291 A | 1/1987 | Bantel et al. |
| 4,677,034 A | 6/1987 | Luthra |
| 4,818,118 A | 4/1989 | Bantel et al. |
| 5,216,808 A | 6/1993 | Martus et al. |
| 5,742,028 A | 4/1998 | Mannava et al. |
| 5,847,825 A | 12/1998 | Alexander et al. |
| 5,885,484 A | 3/1999 | Allison et al. |
| 5,932,120 A | 8/1999 | Mannava et al. |
| 6,005,219 A | 12/1999 | Rockstroh et al. |
| 6,008,896 A | 12/1999 | Sabsabi et al. |
| 6,075,593 A * | 6/2000 | Trantow et al. .............. 356/318 |
| 6,149,389 A | 11/2000 | Hennies et al. |
| 6,159,619 A | 12/2000 | Rockstroh et al. |
| 6,197,424 B1 | 3/2001 | Morrison et al. |
| 6,283,714 B1 | 9/2001 | Rigney et al. |
| 6,380,512 B1 | 4/2002 | Emer |
| 6,452,685 B1 | 9/2002 | Opsal et al. |
| 6,488,986 B1 | 12/2002 | Das et al. |
| 6,532,068 B1 | 3/2003 | Detalle et al. |
| 6,629,464 B1 * | 10/2003 | Suh et al. ...................... 73/602 |
| 2003/0085203 A1 | 5/2003 | Nair et al. |

OTHER PUBLICATIONS

Novelty search report issued from the EP Patent Office (3 pgs.); International Application of: General Electric Company; EP Patent App. No. 04257276.8.

* cited by examiner

*Primary Examiner*—Layla G. Lauchman
(74) *Attorney, Agent, or Firm*—Armstrong Teasdale LLP

(57) ABSTRACT

A method for determining a useful life applied to a coating on a surface of a component coupled to a rotatable member of a rotary machine. The method includes directing a laser across a surface of the component while the rotatable member remains coupled within an assembled rotary machine and measuring radiation emitted from the surface of the component.

26 Claims, 2 Drawing Sheets

METHODS AND APPARATUS FOR EVALUATING ROTARY MACHINERY

BACKGROUND OF THE INVENTION

This application relates generally to turbine engines and, more particularly, to methods and apparatus for determining the useful life of turbine engine component coatings.

At least some known turbine engines include a rotor assembly that includes at least one row of circumferentially spaced rotor blades. Each rotor blade includes an airfoil that includes a pressure side and a suction side connected together at axially spaced leading and trailing edges. Each airfoil extends radially outward from a rotor blade platform. Each rotor blade also includes an attachment portion, such as, a dovetail that extends radially inward from the platform, and is used to mount the rotor blade within the rotor assembly to a rotor disk or spool. At least some known rotor disks include a circumferential dovetail slot that is sized to receive the plurality of rotor blades therein. Known rotor blade dovetails are generally shaped complementary to the disk dovetail slot to enable the rotor blade dovetails and the rotor disk slot to mate together and form a dovetail assembly.

To facilitate protecting against high temperature oxidation and hot corrosion, at least some components of gas turbine engines, such as turbine airfoils, are coated with a barrier coating, for example, a diffusion aluminide coating. Diffusion coatings are imparted by a thermal/chemical reaction process and typically require a reduced or inert atmosphere at an elevated temperature. During the coating process, aluminum migrates to the surface of the coating and reacts with air to form a protective alumina coating.

Conventionally, determining the coating life of a gas turbine part involves measuring the remaining amount of beta aluminide in the protective metal coating on the part. However, this method requires local cutting of the component and metallurgical mounting the region of interest so that it can be etched and optically viewed with a microscope to measure the width of the beta aluminide region. The amount of beta aluminide remaining in the coating is indicative of the amount of aluminum remaining for the production of the alumina protective coating, and is thus used to determine coating life. Accordingly, conventional methods destroy the part and are slow and costly. Moreover, field applications require a replacement part.

BRIEF DESCRIPTION OF THE INVENTION

In one aspect, a method for determining a useful life applied to a coating on a surface of a component coupled to at least one of a rotatable member and a stationary member of a rotary machine. The method includes directing a laser across a surface of the component while the rotatable member remains coupled within an assembled rotary machine and measuring radiation emitted from the surface of the component.

In another aspect, a method for determining a useful life of a coating applied across at least one of a turbine blade component and a turbine nozzle component coupled to a turbine rotor that is rotating coupled in position within an assembled turbine. The method includes vaporizing a portion of the coating applied to at least one of the turbine blade component and the turbine nozzle component using a laser, measuring radiation emitted from the surface of the component being examined to determine the chemical composition of the coating, and calculating the useful life of the coating based on the chemical composition of the coating.

In yet another aspect, a computer program embodied on a computer readable medium for controlling a laser pulse spectrometer system. The computer program including a code segment that receives user selection input data and then remotely instructs the system to vaporize a layer of coating of a component of a turbine with a laser, measure radiation emitted from the surface of the component to determine the chemical composition of the coating, analyze the chemical composition of the coating as a function of depth of the laser and calculate a useful life of the coating of the component.

DETAILED DESCRIPTION OF THE INVENTION

Figure 1:
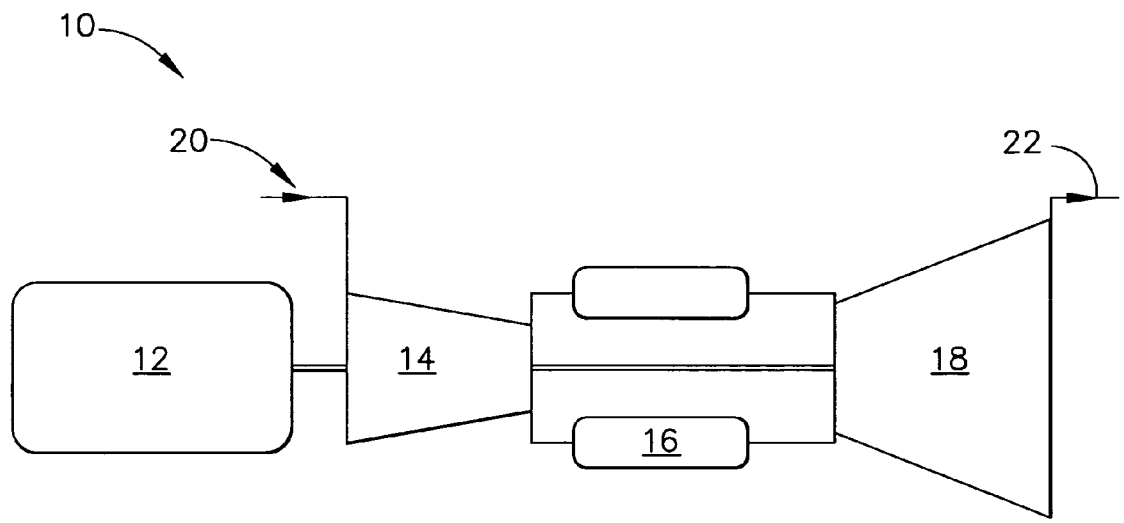
FIG. 1 is a perspective partial cut away view of an exemplary turbine.

FIG. 1 is a schematic illustration of a gas turbine engine 10 including a generator 12, a compressor 14, a combustor 16 and a turbine 18. Engine 10 has an inlet or upstream side 20, and an exhaust or downstream side 22. In one embodiment, engine 10 is a turbine engine commercially available from General Electric Power Systems, Schenectady, N.Y.

In operation, highly compressed air is delivered from compressor 14 to combustor 16. Gas fuel is delivered to the combustor 16 through a plurality of fuel nozzles (not shown in FIG. 1) and hot exhaust gas from combustor 16 is discharged through a turbine nozzle assembly (not shown in FIG. 1) and is used to drive turbine 18. Turbine 18, in turn, drives compressor 14 and generator 12.

Figure 2:
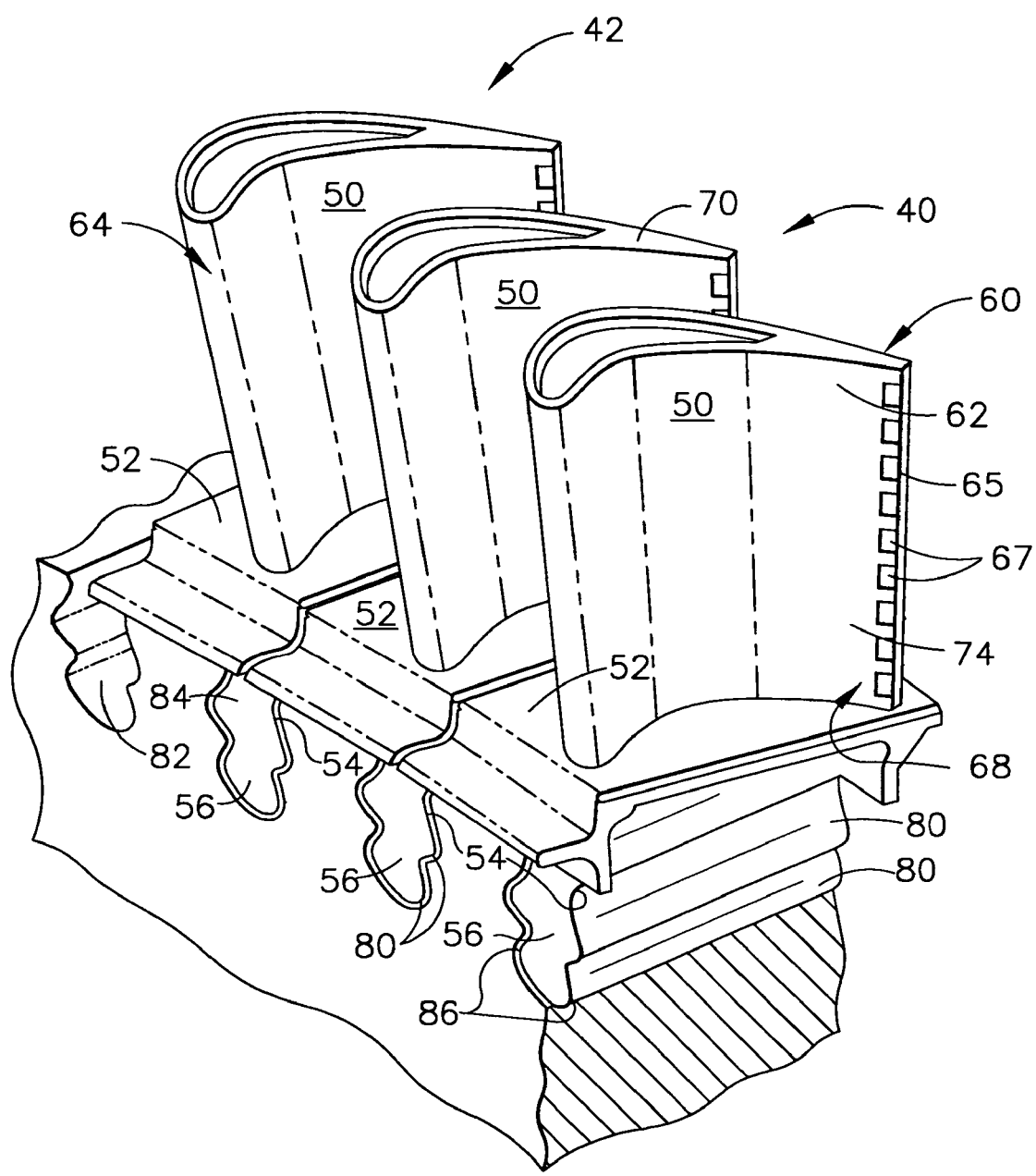
FIG. 2 is a partial perspective view of an exemplary rotor assembly that may be used with the turbine shown in FIG. 1.

FIG. 2 is a perspective view of a rotor assembly 40 that may be used with a turbine, such as turbine engine 10 (shown in FIG. 1). Assembly 40 includes a plurality of rotor buckets or blades 42 mounted to rotor disk 44. In one embodiment, blades 42 form a high-pressure turbine rotor blade stage (not shown) of turbine engine 10. In another embodiment, a plurality of stationary turbine nozzles (not shown) are positioned between adjacent rows of turbine blades 42.

Rotor blades 42 extend radially outward from rotor disk 44, and each blade 42 includes an airfoil 50, a platform 52, a shank 54, and a dovetail 56. Each airfoil 50 includes first sidewall 60 and a second sidewall 62. First sidewall 60 is convex and defines a suction side of airfoil 50, and second sidewall 62 is concave and defines a pressure side of airfoil 50. Sidewalls 60 and 62 are joined at a leading edge 64 and at an axially-spaced trailing edge 65 of airfoil 50. More specifically, airfoil trailing edge 65 is spaced chord-wise and downstream from airfoil leading edge 64. A plurality of trailing edge slots 67 are formed in airfoil 50 to discharge cooling air over trailing edge 65. The cooling air facilitates reducing the temperatures, thermal stresses, and strains experienced by trailing edge 65.

First and second sidewalls 60 and 62, respectively, extend longitudinally or radially outward in span from a blade root 68 positioned adjacent platform 52, to an airfoil tip cap 70. Airfoil tip cap 70 defines a radially outer boundary of an internal cooling chamber (not shown in FIG. 2). The cooling chamber is bounded within airfoil 50 between sidewalls 60 and 62, and extends through platform 52 and through shank 54 and into dovetail 56. More specifically, airfoil 50 includes an inner surface (not shown in FIG. 2) and an outer surface 74, and the cooling chamber is defined by the airfoil inner surface.

Platform 52 extends between airfoil 50 and shank 54 such that each airfoil 50 extends radially outward from each respective platform 52. Shank 54 extends radially inwardly from platform 52 to dovetail 56. Dovetail 56 extends radially inwardly from shank 54 and facilitates securing rotor blade 42 to rotor disk 44. More specifically, each dovetail 56 includes at least one tang 80 that extends radially outwardly from dovetail 56 and facilitates mounting each dovetail 56 in a respective dovetail slot 82. In the exemplary embodiment, dovetail 56 includes an upper pair of blade tangs 84, and a lower pair of blade tangs 86.

Figure 3:
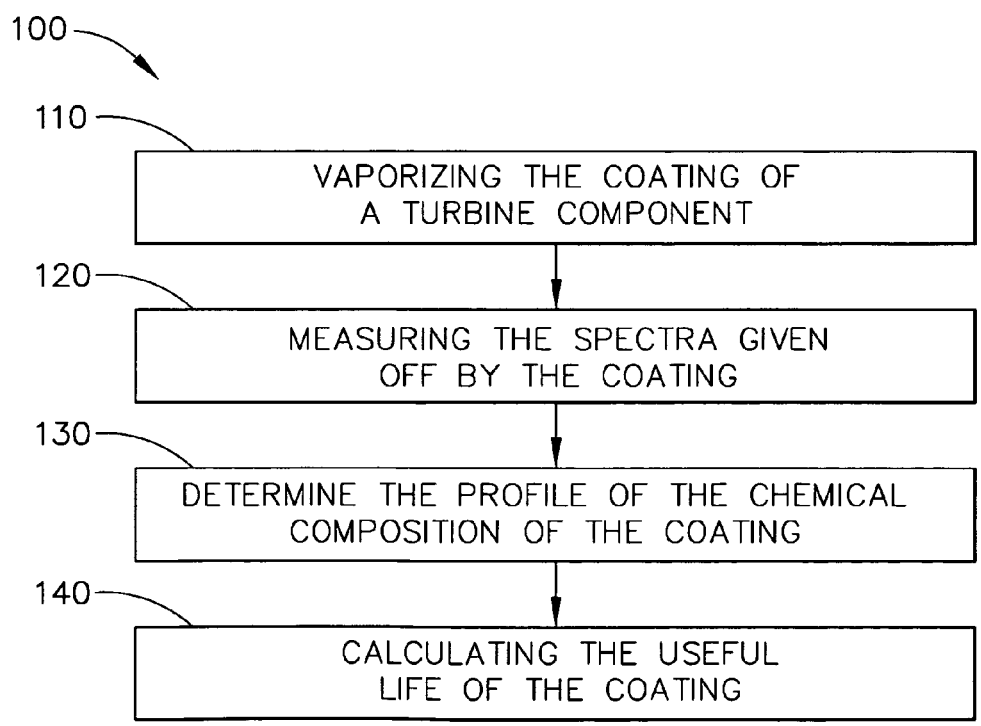
FIG. 3 is a block diagram of a flowchart illustrating an exemplary method for determining the useful life of a component of the rotary machine shown in FIG. 1.

FIG. 3 is a block diagram of a flowchart 100 illustrating an exemplary method of determining a useful life of a turbine component using laser pulse spectroscopy. The method utilizes the characteristic emission of optical radiation or spectra generated from the coating plasma. Initially, a laser is applied or directed across a surface of a turbine component. In one embodiment, the laser is directed across the surface of the component while rotary assembly 40 remains coupled to turbine engine 10. The laser vaporizes 110 a thin layer of coating material to facilitate determining the concentration of the components in the coating. More specifically, each laser pulse removes a thin layer of material during impact with the component's surface. A pulsed laser, such as a neodymium pulsed laser, provides the thermal pulse to vaporize the coating. The thermal pulse is delivered to the part surface using either an optical fiber or an articulating mirror arrangement.

Spectral measurements are produced using an excitation laser method in which the delayed spectroscopic measurements of the laser plasma are used to detect and measure the various specific transient species. More specifically, the delayed measurements are measured relative to the plasma generation pulse. Knowledge of the original elements in the gas turbine protective coatings and substrates is compared to the measurements from the sample to quantitatively determine the concentration of the various elements to estimate composition. The elemental concentration is determined by measuring 120 the intensity of various characteristic spectrum lines emitted from the plasma. In one embodiment, the spectra are measured 120 using a high-speed digital spectrometer.

To facilitate improving the accuracy of determining the weight percent of the aluminum, various combinations of spectra are used. This is useful because the aluminum exists in two stoichiometric phases, i.e., NiAl and $Ni_3Al$. Thus, there is a relationship between the weight percent of aluminum and nickel in the coating. In one embodiment, the method is also used to evaluate metal and ceramic coatings and substrates.

By categorizing the characteristic spectra of coating elements as a function of the depth of plasma, a profile of the chemical composition of the coating is determined 130. Combining this dynamic measurement capability with other exposure data, such as, but not limited to time, temperature, and firing environment, for the coating/substrate combination, the coating life of the part can be calculated. In one embodiment, the coating life is calculated using the design temperature profile of the component. In another embodiment, the measurement of additional elements, such as cobalt, can be utilized to measure temperature.

Once the data is collected, data analysis is performed and the useful coating life is calculated 140. In one embodiment, the useful coating life is calculated 140 utilizing at least one of time data and temperature data. Using a running median reduction of spectral data facilitates generating more accurate estimations of the macro-level of aluminum concentration.

The running median calculation also facilitates reducing 'noise' associated with these coatings as the coating composition varies with depth. However, coating life on a turbine component is dependent on the total amount of aluminum per unit available in the coating on the part. For example, coating depletion can occur in a range of 5–7% weight aluminum. In one embodiment, no reservoir of aluminum is present if the weight percentage of aluminum is under approximately 6%. Thus, additional coating may be applied to the component experiencing coating depletion.

In one embodiment, a computer program is embodied on a computer readable medium for controlling a laser pulse spectrometer system. The computer program includes a code segment that receives user selection input data and then remotely instructs the system to perform the method 100.

During use, the method provides a fast, accurate method of measuring the aluminum content of the metal coating and relating this to the useful life of the coating of the component. Method permits reaching into a remote space such as inside a turbine. In addition, method is capable of remote operation through existing or easily installed inspection ports to the hot gas parts.

The above described method is a cost effective and highly reliable for measuring the aluminum and other elemental concentration in coatings to determine the quantity of beta aluminide available to provide a protective outer coating of alumina on the metal coating. The use of numerical data processing improves the signal to noise ratio of the data and provides better concentration measurements which are needed for coating life determination. In addition, the above described method determines the coating life of a turbine component without damaging the component or destroying a local region of the component.

Exemplary embodiments of laser pulse spectroscopy are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. A method for determining a useful life applied to a coating on a surface of a component coupled to at least one of a rotatable member and a stationary member of a rotary machine, said method comprising:
   directing a laser across a surface of the component while the rotatable member remains coupled within an assembled rotary machine; and
   measuring radiation emitted from the surface of the component.

2. A method in accordance with claim 1 further comprising analyzing the radiation emitted from the surface of the component.

3. A method in accordance with claim 2 wherein analyzing the radiation emitted from the surface of the component further comprises determining the characteristic spectra of the chemical composition of the coating.

4. A method in accordance with claim 1 further comprising calculating the useful life of the coating of the component based on the amount of measured radiation emitted from the component.

5. A method in accordance with claim 4 wherein calculating the useful life of the coating of the component further comprises calculating the percentage of aluminum by weight in the coating.

6. A method in accordance with claim 4 wherein calculating the useful life of the coating of the component further comprises calculating the percentage of nickel by weight in the coating.

7. A method in accordance with claim 1 wherein directing a laser across a surface of the component further comprises vaporizing a layer of coating of the component using the laser.

8. A method in accordance with claim 1 wherein directing a laser across a surface of the component further comprises directing a neodymiam pulsed laser across the surface of the component being examined.

9. A method in accordance with claim 1 wherein measuring radiation emitted from the surface of the component further comprises using a spectrometer to measure the amount of radiation emitted from the surface of the component.

10. A method for determining a useful life of a coating applied across at least one of a turbine blade component and a turbine nozzle component coupled to a turbine rotor that is rotating coupled in position within an assembled turbine, said method comprising:
vaporizing a portion of the coating applied to at least one of the turbine blade component and the turbine nozzle component using a laser;
measuring radiation emitted from the surface of the component being examined to determine the chemical composition of the coating;
calculating the useful life of the coating based on the chemical composition of the coating.

11. A method in accordance with claim 10 wherein vaporizing a portion of the coating applied to at least one of the turbine blade component and the turbine nozzle component further comprises vaporizing a layer of the coating using a neodymiam pulsed laser.

12. A method in accordance with claim 10 wherein measuring radiation emitted from the surface of the component further comprises measuring radiation emitted from the surface of the component using a digital spectrometer.

13. A method in accordance with claim 10 wherein measuring radiation emitted from the surface of the component further comprises measuring the intensity of characteristic spectrum lines emitted from the coating.

14. A method in accordance with claim 10 further comprising determining an amount of beta aluminide in the coating.

15. A method in accordance with claim 10 wherein calculating the useful life of the coating of the component further comprises calculating the useful life of the coating as a function of at least one of time and temperature.

16. A method in accordance with claim 10 further comprising applying additional coating to the component based on the chemical composition.

17. A laser pulse spectrometer system comprising a computer program embodied on a computer readable medium for controlling said laser pulse spectrometer system, said computer program comprising a code segment that receives user selection input data and then remotely instructs said system to:
vaporize a layer of coating of a component of a turbine with a laser;
measure radiation emitted from the surface of the component to determine the chemical composition of the coating;
analyze the chemical composition of the coating as a function of depth of the laser; and
calculate a useful life of the coating of the component.

18. A laser pulse spectrometer system in accordance with claim 17 further configured to measure radiation emitted from the surface of the component using a digital spectrometer.

19. A laser pulse spectrometer system in accordance with claim 17 further configured to vaporize a layer of coating of a component of a turbine using a neodymiam pulsed laser.

20. A laser pulse spectrometer system in accordance with claim 17 further configured to determine the characteristic spectra of the chemical composition of the coating.

21. A laser pulse spectrometer system in accordance with claim 17 further configured to calculate the percentage of aluminum by weight in the coating.

22. A computer program embodied on a computer readable medium for controlling a laser pulse spectrometer system, said computer program comprising a code segment that receives user selection input data and then remotely instructs said system to:
vaporize a layer of coating of a component of a turbine with a laser;
measure radiation emitted from the surface of the component to determine the chemical composition of the coating;
analyze the chemical composition of the coating as a function of depth of the laser; and
calculate a useful life of the coating of the component.

23. A computer program in accordance with claim 22 further configured to measure radiation emitted from the surface of the component using a digital spectrometer.

24. A computer program in accordance with claim 22 further configured to vaporize a layer of coating of a component of a turbine using a neodymiam pulsed laser.

25. A computer program in accordance with claim 22 further configured to determine the characteristic spectra of the chemical composition of the coating.

26. A computer program in accordance with claim 22 further configured to calculate the percentage of aluminum by weight in the coating.

* * * * *

UNITED STATES PATENT AND TRADEMARK OFFICE
CERTIFICATE OF CORRECTION

PATENT NO.       : 7,064,825 B2  Page 1 of 1
APPLICATION NO.  : 10/722298
DATED            : June 20, 2006
INVENTOR(S)      : Viertl et al.

It is certified that error appears in the above-identified patent and that said Letters Patent is hereby corrected as shown below:

In Claim 8, column 5, line 23, delete "neodymiam" and insert therefor -- neodymium --.
In Claim 11, column 5, line 47, delete "neodymiam" and insert therefor -- neodymium --.
In Claim 19, column 6, line 26, delete "neodymiam" and insert therefor -- neodymium --.
In Claim 24, column 6, line 51, delete "neodymiam" and insert therefor -- neodymium --.

Signed and Sealed this

Twenty-seventh Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 7,064,825 B2
APPLICATION NO. : 10/722298
DATED : June 20, 2006
INVENTOR(S) : Viertl et al.

It is certified that error appears in the above-identified patent and that said Letters Patent is hereby corrected as shown below:

In Claim 8, column 5, line 23, delete "neodymiam" and insert therefor -- neodymium --.
In Claim 11, column 5, line 47, delete "neodymiam" and insert therefor -- neodymium --.
In Claim 19, column 6, line 26, delete "neodymiam" and insert therefor -- neodymium --.
In Claim 24, column 6, line 51, delete "neodymiam" and insert therefor -- neodymium --.

Signed and Sealed this

Eleventh Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,064,825 B2 Page 1 of 1
APPLICATION NO. : 10/722298
DATED : June 20, 2007
INVENTOR(S) : Viertl et al.

It is certified that error appears in the above-identified patent and that said Letters Patent is hereby corrected as shown below:

Title page item [75] inventor add--

--PAMELA K. BENICEWICZ--

Signed and Sealed this

Fifteenth Day of April, 2008

JON W. DUDAS
*Director of the United States Patent and Trademark Office*

UNITED STATES PATENT AND TRADEMARK OFFICE
CERTIFICATE OF CORRECTION

PATENT NO.        : 7,064,825 B2
APPLICATION NO.   : 10/722298
DATED             : June 20, 2006
INVENTOR(S)       : Viertl et al.

It is certified that error appears in the above-identified patent and that said Letters Patent is hereby corrected as shown below:

Title page item [75] inventor add--

--PAMELA K. BENICEWICZ--

This certificate supersedes the Certificate of Correction issued April 15, 2008.

Signed and Sealed this

Sixth Day of May, 2008

JON W. DUDAS
*Director of the United States Patent and Trademark Office*